United States Patent [19]

Dutcher et al.

[11] Patent Number: 5,143,090
[45] Date of Patent: Sep. 1, 1992

[54] CARDIAC LEAD

[75] Inventors: Robert G. Dutcher; John C. Hill; Robert J. Scott, all of Minneapolis, Minn.

[73] Assignee: Possis Medical, Inc., Minneapolis, Minn.

[21] Appl. No.: 707,681

[22] Filed: May 30, 1991

Related U.S. Application Data

[60] Continuation-in-part of Ser. No. 600,627, Oct. 22, 1990, Pat. No. 5,040,545, which is a division of Ser. No. 430,596, Nov. 2, 1989, Pat. No. 4,972,847.

[51] Int. Cl.$^5$ .............................................. A61N 1/00
[52] U.S. Cl. .............................. 128/785; 128/419 P; 128/790
[58] Field of Search ............. 128/785, 786, 419 P, 128/784, 783, 790

[56] References Cited

U.S. PATENT DOCUMENTS

| | | | |
|---|---|---|---|
| 3,543,761 | 12/1970 | Bradley | 128/785 |
| 3,737,579 | 6/1973 | Bolduc | 128/785 |
| 3,749,101 | 7/1973 | Williamson | 128/419 P |
| 3,827,428 | 8/1974 | Hon et al. | 128/642 |
| 3,875,947 | 4/1975 | Jula et al. | 128/785 |
| 4,010,758 | 3/1977 | Rockland et al. | 128/419 P |
| 4,011,861 | 3/1977 | Enger | 128/642 |
| 4,033,357 | 7/1977 | Helland et al. | 128/785 |
| 4,146,037 | 3/1979 | Flynn et al. | 128/419 P |
| 4,149,542 | 4/1979 | Thoren | 128/786 |
| 4,207,903 | 6/1980 | O'Neill | 128/785 |
| 4,271,846 | 6/1981 | Little | 128/785 |
| 4,355,642 | 10/1982 | Alferness | 128/785 |
| 4,357,946 | 11/1982 | Dutcher et al. | 128/785 |
| 4,502,492 | 3/1985 | Bornzin | 128/785 |
| 4,603,704 | 8/1986 | Mund et al. | 128/419 P |
| 4,641,656 | 2/1987 | Smits | 128/419 D |
| 4,750,977 | 6/1988 | Marrese | 205/148 |

Primary Examiner—Francis Jaworski
Assistant Examiner—George Manuel
Attorney, Agent, or Firm—Burd, Bartz & Gutenkauf

[57] ABSTRACT

A cardiac lead for transmitting electric current to the heart and/or sensing and monitoring electrical activity of the heart has an elongated electrical conductor connected to a head. An electrode mounted on the head comprises a helical wire adapted to be turned into heart tissue. A second electrode having an irregular or non-flat surface surrounds the helical wire. The non-flat surface may be a wire mesh, a segmented plate and an annular plate supporting one or more coiled wires.

40 Claims, 11 Drawing Sheets

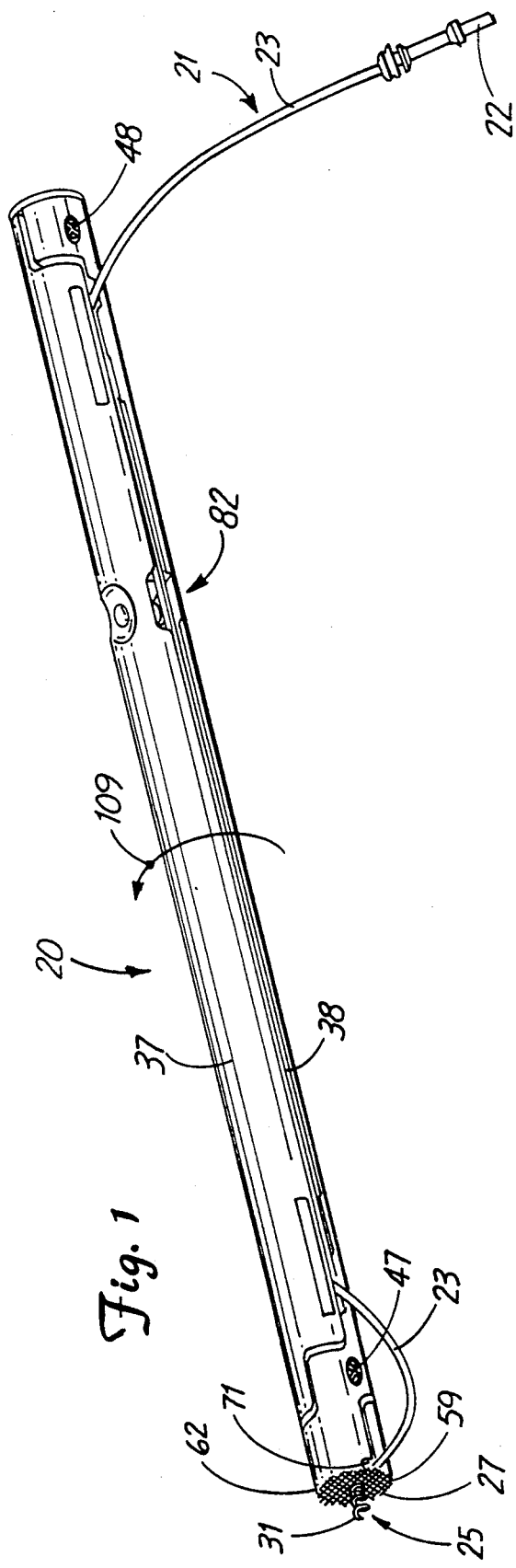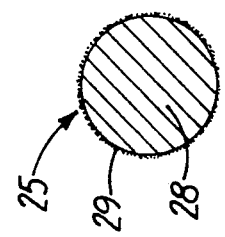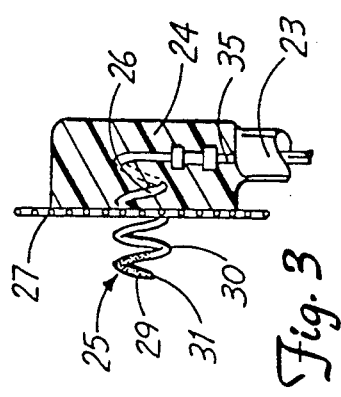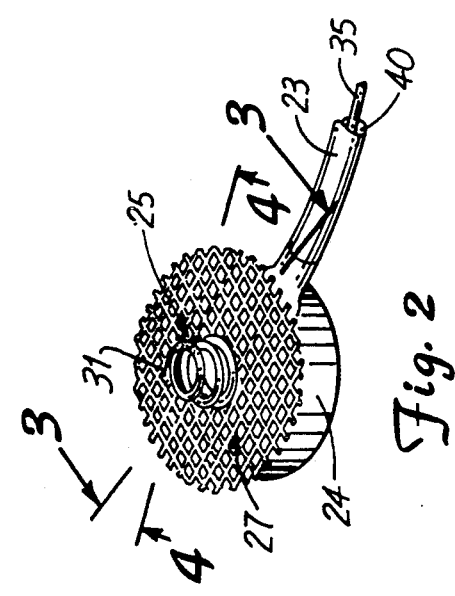

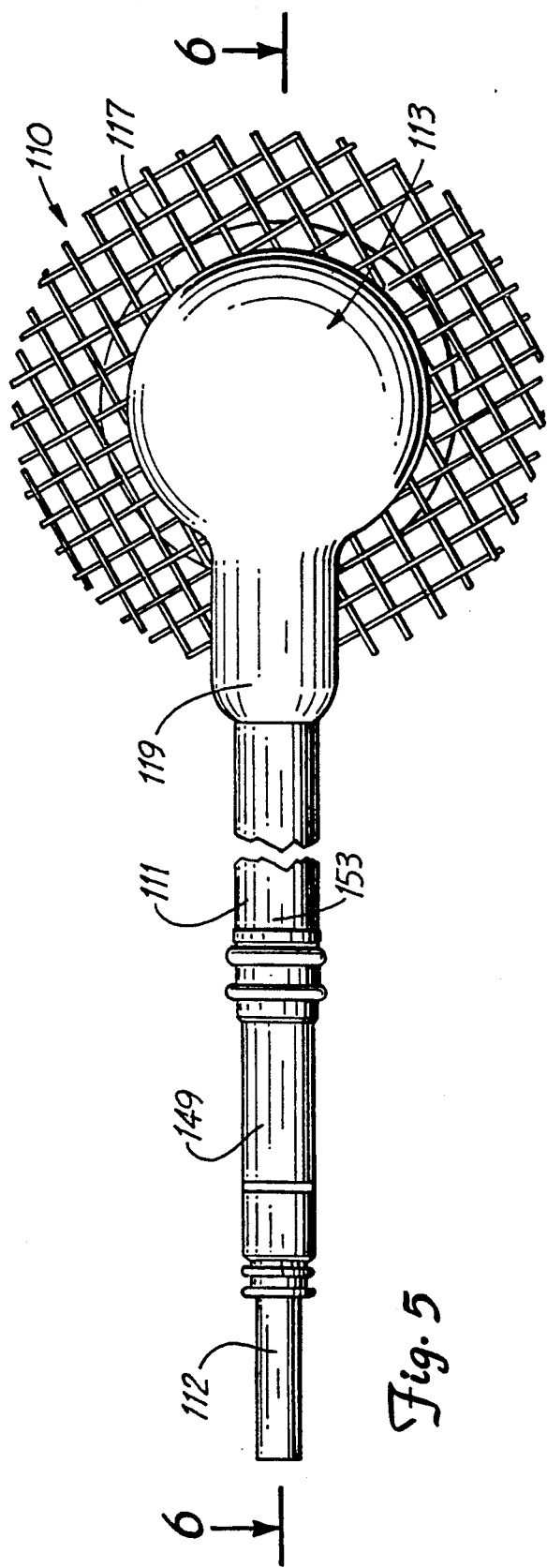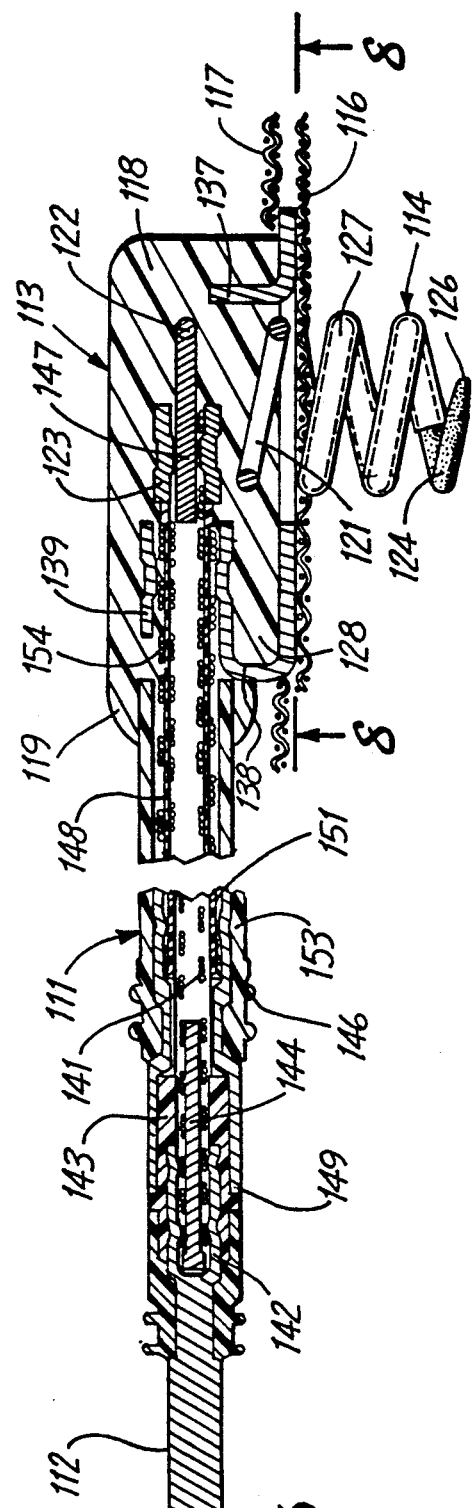
Fig. 5
Fig. 6

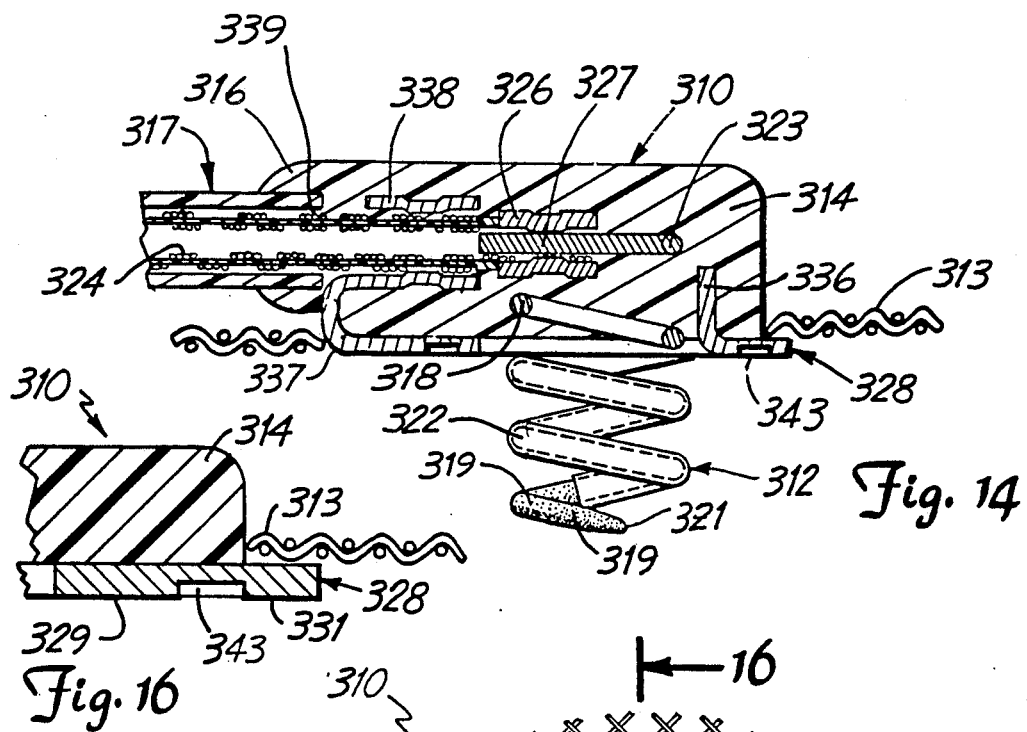
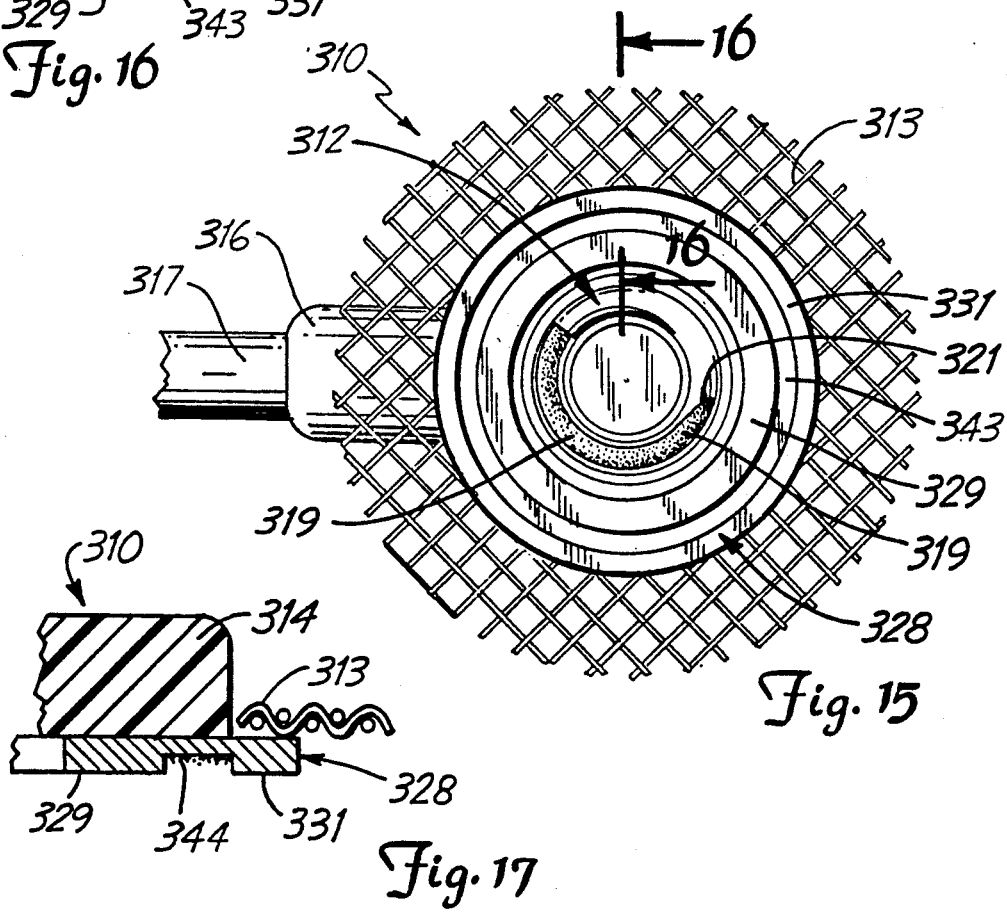

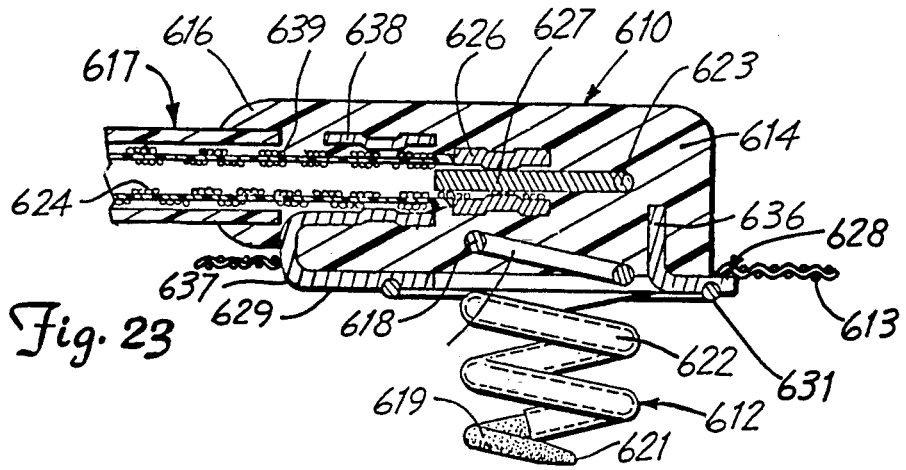
Fig. 23
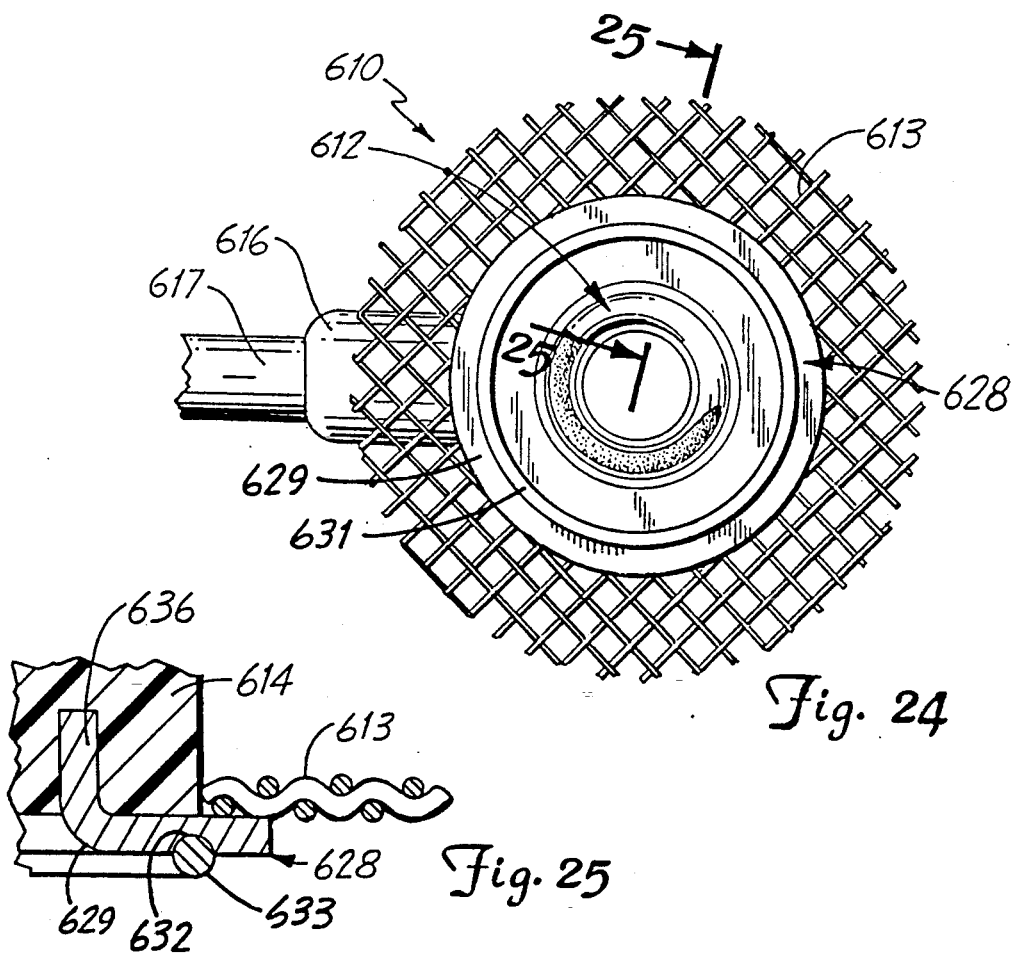
Fig. 24
Fig. 25

CARDIAC LEAD

CROSS REFERENCE TO RELATED APPLICATION

This Application is a continuation-in-part of U.S. Application 600,627 filed Oct. 22, 1990 now U.S. Pat. No. 5,040,545. Application Ser. No. 600,627 is a division of U.S. application Ser. No. 430,596 filed Nov. 2, 1989, now U.S. Pat. No. 4,972,847.

FIELD OF INVENTION

The invention relates to cardiac leads connectable to a heart for transmitting electric current to the heart and monitoring the electrical activity of the heart.

BACKGROUND OF THE INVENTION

Myocardial leads having rigid helical coils that are turned into heart tissue are disclosed by L. R. Bolduc in U.S. Pat. No. 3,737,579. The helical coils are connected with an elongated flexible conductor to a pacemaker for transmitting electrical pacing currents to the heart. A bipolar electrode having a helical electrode and an annular plate electrode to establish an electrical field through the heart tissue to ensure efficient stimulation of the tissue and minimum current drainage of the power supply of the pacemaker is disclosed by Rockland et al in U.S. Pat. No. 4,010,758. Other types of bipolar electrodes are disclosed by Fischell in U.S. Pat. No. 4,125,116 and Alferness in U.S. Pat. No. 4,355,642. These patents show tissue stimulation electrodes structure having central electrode surrounded by secondary electrodes for applying pacing and defibrillation pulses to the heart.

SUMMARY OF THE INVENTION

The invention relates to a cardiac lead connectable to an implantable cardiac arrhythmia management device (not shown) for transmitting electric current to the heart and/or sensing and monitoring the electrical activity of the heart. The implantable cardiac arrhythmia management device includes but is not limited to cardiac pacemakers and automatic implantable cardiac defibrillators (AICD). The lead has an elongated flexible conductor enclosed within a sheath of nonelectrically conductive material to electrically connect the cardiac management device with one or more electrodes adapted to be implanted in or on heart tissue. The electrodes are supported on a head of non-electrically conductive material and joined to the conductor. In one form of the invention the electrode is a helical wire having a portion located externally of the head adapted to be turned into the heart tissue to secure the lead to the heart tissue and transmit pace-making electrical signals thereto or receive electrical signals therefrom. The helical wire has a sheath of non-electrically conductive material surrounding the wire except for a distal portion thereof which represents the electrode. The external portion of the electrode has an outer surface covered with a layer of platinum black particles. The layer of platinum black particles has substantially uniform particle size and uniform particle distribution on the outer surface of the distal portion of the electrode thereby the layer of platinum black particles has a uniform microporous outer surface being in contact with the heart tissue to decrease electrical losses at the electro-tissue interface, increase the current density to the heart tissue, establish intimate contact between the electrode and myocardium tissue, lower stimulation thresholds, and increase amplitude of electrical signals from the myocardium.

The invention includes a bipolar electrode having a coaxial conductor attached to a head supporting a first electrode adapted to be connected to the myocardium of a heart and a second electrode surrounding the helical electrode engageable with the epicardium and/or myocardium when the first electrode is in contact with the heart tissue. The first electrode has an outer sharpened or pointed end portion with a surface that can be coated with platinum black particles. The second electrode is an anode or annular member of electrically conductive metal, such as titanium, platinum, or platinum iridium, having an irregular or non-flat surfaces that can be coated with platinum black particles which contact the heart tissue. Other types of coatings including but not limited to pyrolytic carbon, titanium nitride, and other surfaces can be used to enhance the electro-tissue interface between the second electrode and heart tissue. The combined areas of the surfaces of the second electrode are substantially larger than the area of the surface of the end portion of the first electrode to maximize voltage applied to the heart and minimize electrical resistance between the anode and the heart tissue. The electrical coaxial conductor contains two elongated coil wires that are separately attached to the first electrode and the second electrode. The combined areas of the heart contact surfaces of the second electrode is greater than a flat surface and allows for tissue ingrowth to securely hold the second electrode to the heart tissue. The concentric arrangement of the second electrode around the first electrode provides electrical sensing vectors in all directions.

The irregular or non-flat heart contact surfaces can take a number of configurations, such as a wire mesh connected to an annular support plate, an annular plate having segmented grooves, one or more annular grooves, or holes, and an annular plate supporting one or more rings or one or more annular coiled wires. The irregular heart contact surfaces or portions of these surfaces can be coated with platinum black particles, platinum, pyrolytic carbon, titanium nitride or other surface treatment to enhance the electrode-tissue interface of the second electrode and heart tissue.

These and other objects and advantages of the cardiac lead of the invention are embodied in the following detailed description and drawings.

DESCRIPTION OF DRAWING

FIG. 1 is a perspective view of a cardiac lead insertion tool holding an implantable lead having a myocardial helical electrode;

FIG. 2 is a perspective view of the distal end of the lead shown in FIG. 1;

FIG. 3 is a sectional view taken along line 3—3 of FIG. 2;

FIG. 4 is an enlarged sectional view taken along line 4—4 of FIG. 2;

FIG. 5 is a forshortened plan view of a bipolar cardiac lead having a helical electrode surrounded by a second wire mesh electrode;

FIG. 6 is a sectional view taken along line 6—6 of FIG. 5;

FIG. 14 is a sectional view similar to FIG. 11 of a second modification of the bipolar cardiac lead of the invention;

FIG. 15 is a bottom view of the distal end of the of FIG. 14;

FIG. 16 is an enlarged sectional view taken along the line 16—16 of FIG. 15;

FIG. 17 is a sectional view similar to FIG. 16 showing platinum black particles on the second electrode;

FIG. 23 is a sectional view similar to FIG. 11 of a fifth modification of the bipolar cardiac lead of the invention;

FIG. 24 is a bottom view of the distal end of the lead of FIG. 23;

FIG. 25 is an enlarged sectional view of a portion of the bipolar lead of FIG. 23 showing an alternative mounting of the second electrode ring;

Referring to FIG. 1, there is shown the myocardial lead installation tool known as an introducer, indicated generally at 20, holding a cardiac lead, indicated generally at 21, prior to the implantation of the electrode of the lead into the myocardium of a heart. Introducer 20 is disclosed in U.S. Pat. No. 4,972,847, incorporated herein by reference. Lead 21 has a connector 22 at the proximal end thereof adapted to be connected to terminal of a pacemaker that generates heart pacing currents. Connector 22 is joined to an elongated flexible electrical conductor 23 having a distal end joined to a generally cylindrical head 24. Head 24 is made of non-electrical conductive material that is biocompatible, such as medical grade silicone rubber. A rigid helical electrode 25 having several convolutions is mounted on the center of head 24. As shown in FIG. 3, electrode 25 has an end 26 embedded in head 24 and connected to conductor wire 35 of conductor 23. Wire 35 is a multifilar conductor coil made of nickel cobalt wire or other suitable conducting material. Wire 35 is enclosed within non-electrical conductive sheath 40 that is biocompatible, such as medical grade silicone rubber. A generally flat circular netting 27 surrounds electrode 25. Netting 27 is joined to head 24 by bonding it directly to the rubber material of head 24 or suitable connecting materials. The outer peripherial edge of netting 27 projects radially outward from head 24 to increase the surface engagement with the heart tissue. Netting 27 can be porous polyester fiber that enhances fibroic growth to insure a secure connection of electrode 25 to the heart tissue.

Helical electrode 25 is a rigid helical wire 28 terminating in a pointed or sharpened end 31. A sheath 30 of non-electrical conductive material, such as medical grade silicone rubber, covers wire 28 except for about the end one half turn portion thereof, such as between 160 and 190 degrees of the end portion of wire 28. This end portion of wire 28 comprises the active electrode. Wire 28 can be made of a platinum/iridium. The entire exposed exterior surface of the end one half turn section of wire 28 is completely covered with a coat or layer of platinum black particles to substantially reduce electrode polarization. Wire 28 is platinized to develop the coating of platinum black particles 29. The platinum black particles have a micro porous surface of submicron size particles. The platinum black particles 29 are electrochemically plated onto the outer surface of the wire or substrate 28. The exterior end portion of wire 28 is placed in a platinum ion plating solution and subjected to an electric d.c. current. The plating solution and wire 28 are also subjected to intermittent ultrasonic vibrations that agitate the platinum ions. The electric current is terminated during the vibration period. The time period between vibration episodes can be varied. An oscillating piezoelectric ceramic is used to generate vibrations at a selected frequency that produces uniform particle size and particle distribution. The submicron size particles of platinum black 29 are bonded to the entire outside surface of wire 28 up to head 24 as seen in FIG. 4. The platinum black particles 29 have substantially uniform particle size and particle distribution resulting in uniform current density over the layer of platinum black particles 29 and lower stimulation thresholds. The current carried by lead 21 is delivered to the heart muscle almost exclusively through the platinum black particles 29. As shown in FIG. 3 and 4, the layer of platinum black particles 29 has a continuous microporous surface which provides for intimate contact between the end portion 29 of electrode 25 and the myocardial tissue and an increase in real surface area with a resulting decrease in electrode-tissue interface electrical losses and maximize voltage applied to the simulatable tissue of the heart and thereby lower stimulation thresholds and increase intracardiac electrical signal sensing.

Figure 7:
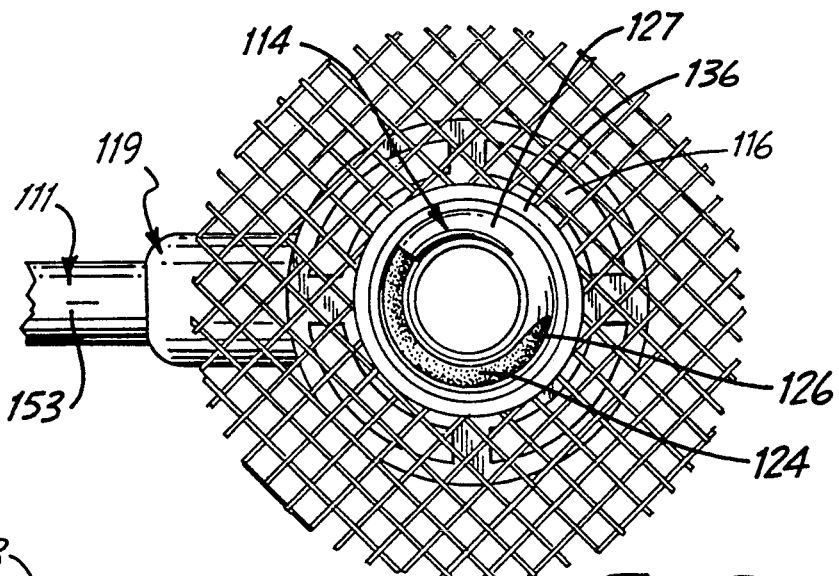
FIG. 7 is a bottom view of the distal end of the electrode of FIG. 5.
Figure 9:
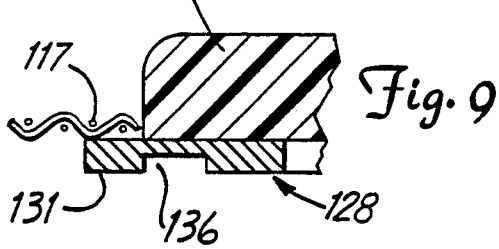
FIG. 9 is an enlarged sectional view taken along line 9—9 of FIG. 8.
Figure 8:
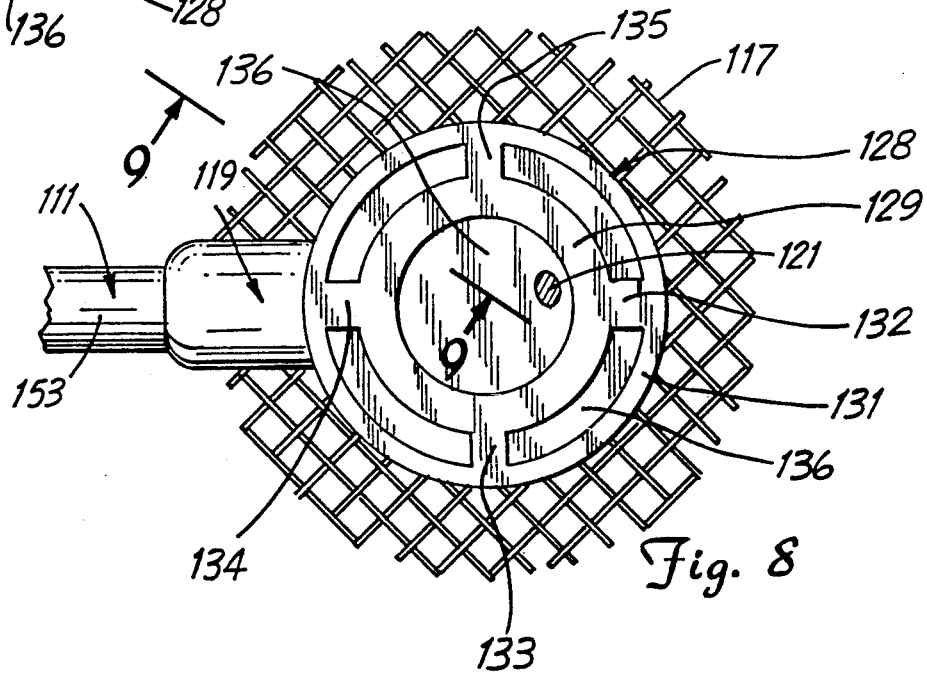
FIG. 8 is a sectional view taken along line 8-8 of FIG. 6.
Figure 10:
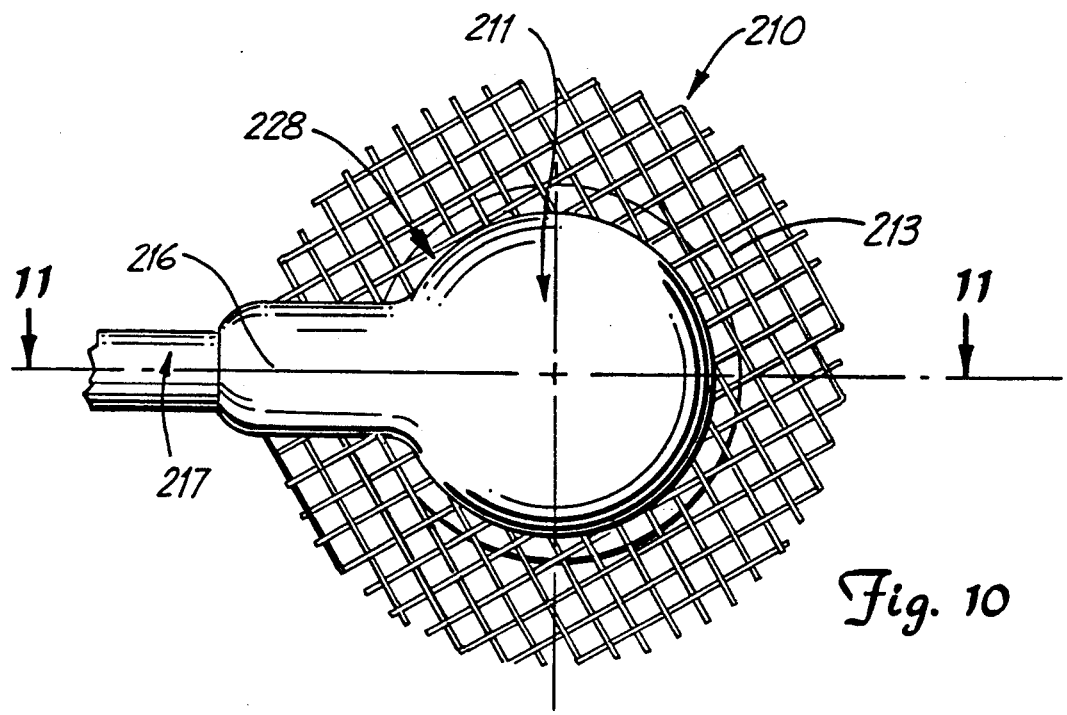
FIG. 10 is a forshortened plan view of a first modification of the bipolar cardiac lead of the invention.

Returning to FIG. 1, introducer 20 has a pair of elongated beams 37 and 38 pivotly connected at their opposite ends with pivot members 47 and 48. The distal ends of beams 37 and 38 have a pair of arcuate jaws 59 and 62 for gripping opposite sides of head 24 of lead 21. Beams 37 and 38 have a slot 71 adjacent jaws 59 and 62 which allows conductor 23 to be located between beams 37 and 38. A releasable lock mechanism indicated generally at 82 holds the beams 37 and 38 to a closed position to maintain the gripping force of jaws 59 and 62 on head 24. Releasable lock mechanism 82 can be disengaged to allow beams 37 and 38 to move to an open position releasing the grip of jaws 59 and 62 on head 24. Introducer 20 is rotated in the direction of the arrow 109 during the implant procedure of helical electrode 25. Only a small keyhole opening in the chest wall is required to implant the lead. The detailed structure and operation of introducer 20 is disclosed in U.S. Pat. No. 4,972,847, incorporated herein by reference.

Referring to FIGS. 5 to 8, there is shown a bipolar cardiac lead indicated generally at 110 for monitoring the electrical activity of a heart and transmitting pacing currents to the heart. Lead 110 has an elongated flexible conductor 111 terminating in a connector 112. Connector 112 has a cylindrical shape adapted to be connected to a demand pacemaker that functions in response to sensed electrical signals from the heart and generates heart pacing currents as required. Conductor 111 has a distal end joined to a generally cylindrical head 113. Head 113 is made of non-electrical conductive biocompatible material, such as medical grade silicone rubber. A rigid helical electrode 114 projects downwardly from head 113. Electrode 114 is a cathode. A second annular anode electrode 116 or anode surrounds the helical electrode 114. A netting 117 joined to head 113 surrounds lower end of head 113 and extends radially outwardly therefrom to increase the surface area engagement of electrode 116 with the epicardium. Electrode 116 has non-flat surfaces locatable in intimate electrical contact with heart tissue. A netting 117 is a porous polyester fiber that enhances fibrotic growth is secured to head 113 to insure a secure connection of electrodes 114 and 116 to the heart tissue.

Head 113 has a cylindrical rubber body 118 having a laterally projected member 119 joined to conductor 111. Electrode 114 has a helical or coil shaped wire 121 having an inner end 122 embedded within the rubber material of body 118. A short rod or pin 147 extended into a sleeve 123 electrically connects wire 121 with sleeve 123, as shown in FIG. 6. Wire 121 can have an end extended into sleeve 123. The opposite or outer end 124 of wire 121 terminates in a pointed or sharpened tip 126. The last one half turn portion of end 124 is competely covered with a coat or layer of platinum black particles such as platinum black particles 29 referred to in FIGS. 3 and 4. A sheath or coating 127 of non-electrical conductive material, such as medical grade silicone rubber, covers wire 121 from head 118 to the end 124 containing the platinum black particles.

As shown in FIGS. 6 and 7, second electrode 116 includes a support or washer-like member 128 attached to the bottom 136 of body 118. Support 128 has a pair of concentric rings 129 and 131 joined with generally radial spokes 132 to 135. Support 128 can be titanium that is joined or bonded to porous electrode 116. Ring 131 projects radially outward from the base of body 118 to provide annular support for electrode 116. Support 128 has an upwardly directed tab 137 embedded in the material of body 118. Diametrically opposite of tab 137 is an upwardly directed ear 138 terminating in a generally cylindrical sleeve 139 concentric with and laterally spaced from sleeve 123.

An elongated conductor coil 141 has a proximal end extended into a sleeve 142 connected to connector 112. A plastic cylinder 143 surrounds sleeve 142 and accommodates a central pin 144 located within coil 141 and extended into sleeve 142 to fix coil 141 to sleeve 142. Coil 141 is located within an elongated rubber sheath 146 that extends to sleeve 123 located in head 113. Second pin 147 or the straight inner end of wire 122 located within the distal end of coil 141 extends through sleeve 123 to secure coil 141 to sleeve 123 and connect coil 141 to the inner end 122 of helical electrode 114 thereby making a continuous electrical connection between connector 112 and electrode 114.

A second conductor coil 148 surrounds sheath 146. Coil 148 has a proximal end located within a metal conductor tube 149. Reinforcement sleeve or tubular member 151 located within coil 148 around the outside sheath 146 holds coil 148 in engagement with inner end of tube 149. Coil 148 is surrounded with an outer flexible rubber sheath 153 of non-electrically conductive medical grade rubber which is located over part of tube 149 and connected to member 119. A sleeve 154 located within the distal end of coil 148 holds coil 148 into engagement with sleeve 139 thereby providing an electrical connection between tube 149 and the second electrode 116.

Introducer 20 is used to turn the helical electrode 114 into the heart tissue. The jaws 59 and 62 of introducer 20 grip the head 113. Introducer 20 is locked onto head 114 and then rotated to turn helical electrode 114 into the heart tissue. The porous electrode 116 is retained in intimate surface contact with the heart tissue. The electrode 116 and netting 117 being porous enhances tissue ingrowth to firmly fix head 118 to the heart tissue.

Referring to FIGS. 10 to 13, there shown a first modification of the bipolar cardiac lead indicated generally at 210. Lead 210 has an elongated flexible coaxial conductor 217 having a connector (not shown) such as connector 112 shown in FIGS. 5 and 6. Lead 210 has a head 211 supporting a first electrode 212, a second electrode 228 and a netting 213. Head 211 has a cylindrical body 214 of biocompatable material, such as silicone rubber, surrounding the inner end of the electrode 212. Body 214 has a lateral member 216 secured to conductor 217.

Electrode 212 has a coil wire 218, such as a platinum or platinum iridium wire, having an exposed outer end 219 terminating in a sharp point 221. Outer end portion 219 is covered with a coating of platinum black particles. The coating or layer of platinum black particles has a substantially uniform particle size and uniform distribution over the entire outer surface of the outer end portion 219 which in use is placed in a uniform microscopic surface in contact with the heart tissue. This decreases the electrical losses and increases the amplitude of electrical signals from the myocardium. The portion of the wire 218 from body 214 to end 219 is enclosed within a sheath or coating 222 of medical grade rubber which electrically insulates this portion of the wire from the heart tissue. The inner end 223 of wire 218 is embedded within body 214 and is in electrical engagement with the first or inner conductor coil 224. Coil 224 is in contact with a sleeve 226 embedded within body 214. A pin 227 located within coil 224 holds coil 224 in engagement with sleeve 226. Pin 227 can be at the end of wire 218.

Figure 11:
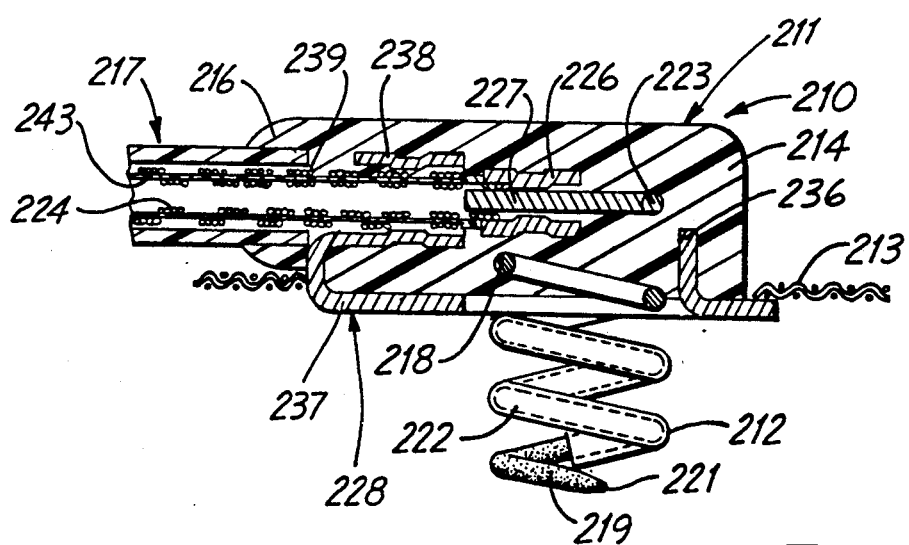
FIG. 11 is a sectional view taken along line 11—11 of FIG. 10.
Figure 12:
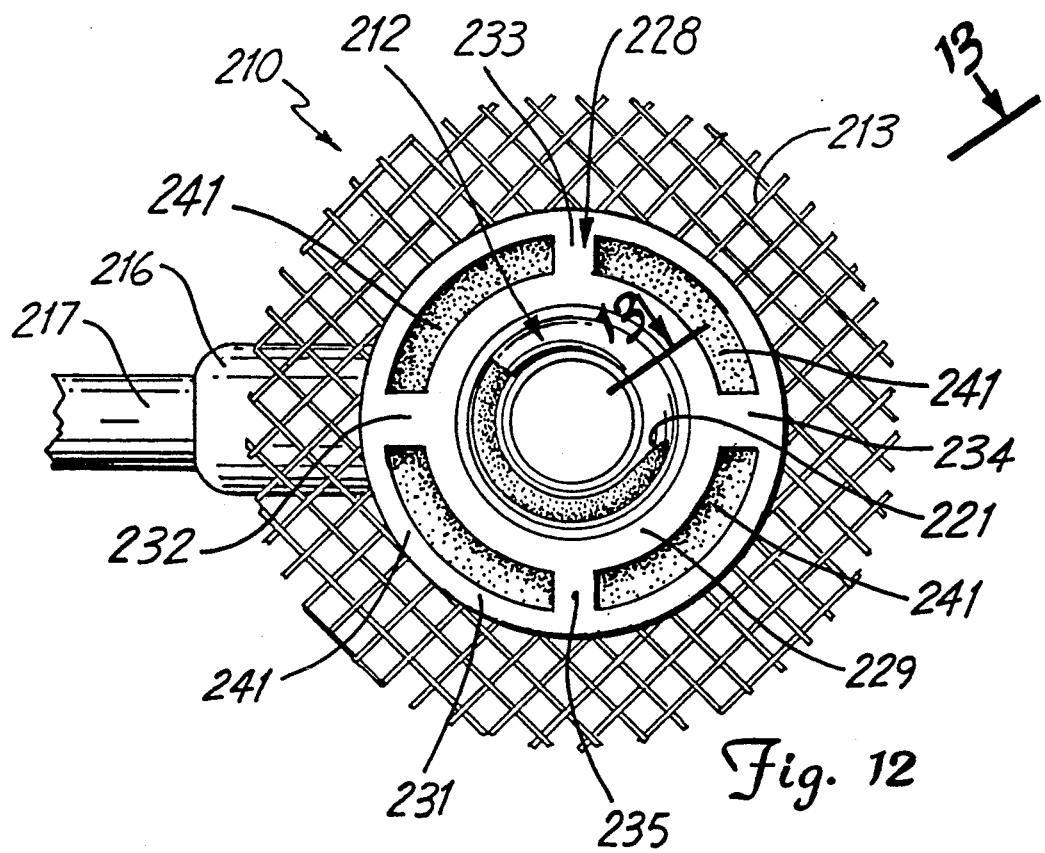
FIG. 12 is a bottom view of the distal end of the electrode of FIG. 10.
Figure 13:
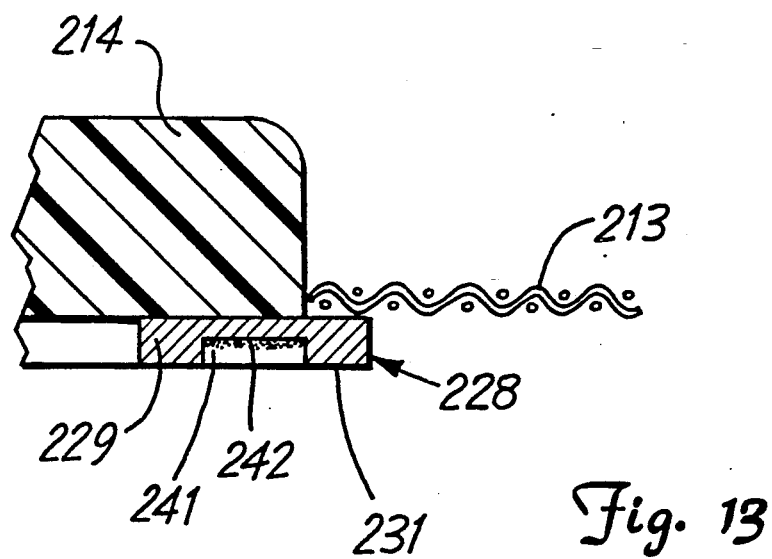
FIG. 13 is an enlarged sectional view taken along the line 13—13 of FIG. 12.

As shown in FIGS. 11 and 12, the second electrode indicated generally at 228 is an anode mounted on the bottom of body 214. Member 228 is a toroidal metal member having stepped outer surfaces adapted to engage the heart tissue. The entire outer surface of member is not flat thereby providing increased surface area as compared to a flat surface. Member 228 has a pair of concentric rings 229 and 231 connected with radial spokes 232-235. Spokes 232-235 are separated from each other with segment or arcuate grooves 241. As shown in FIG. 12, four circumferentially spaced grooves 241 are open to the outside or contact surface of the electrode 228. As shown in FIG. 13, the bottom surfaces of the grooves 241 are coated with platinum black particles 242. The coating can be platinum or iridium. All of the outer surfaces of electrode 228 can be coated with platinum black partcles, platinum or iridium to increase the surface area of the electrode 228 that engages the heart tissue. Other surface treatments including but not limited to Pyrolite carbon and Titanium nitride can be used to enhance the electro-tissue interface between the second electrode 228 and heart tissue. An upwardly directed tab 236 embedded in body 214 is joined to one side of ring 229 aligned with spoke 234. Diametrically opposite tab 236 is an upwardly directed ear 237 joined to a sleeve 238 surrounding the distal end of conductor 217. A second coil 239 located about an insulation or plastic tube 243 surrounding first coil 224 fits into sleeve 238. An expansion insert located about the plastic tube 243 holds the second coil in engagement with sleeve 238 thereby electrically connecting second coil 239 with the second electrode 228. As shown in FIGS. 12 and 13, electrode 228 has a diameter greater than the diameter of body 214. An outer peripheral annular portion of electrode 228 extends radially outward from body 214. Electrode 228 is made of titanium or like conductive biocompatible materials having a coating of platinum black particles or a coating of platinum or iridium. The non-flat outside surface construction of electrode 228 increases the surface contact area with a heart tissue and provides for effective sensing vector in all directions.

Referring to FIGS. 14 to 17 there is shown a second modification of the bi-polar cardiac lead indicated generally at 310. The parts of lead 310 that correspond to the cardiac lead 210 have the same reference numbers with the suffix 3 in lieu of 2. Lead 310 has an elongated flexible coaxial conductor that is adapted to be connected to a pulse generator (not shown). The distal end of lead 310 has a head 311 supporting a first electrode indicated generally a 312 comprising a cathode and a second electrode indicated generally at 328 comprising an anode. The second electrode 328 surrounds electrode 312 and is secured to a body 314. The body 314 is a biocompatable material, such as silicon rubber, that supports the inner end of the helical electrode 312. Body 314 has a lateral member or nipple 316 secured to coaxial conductor 317.

Electrode 312 has a wire coil 318, such as a platinum or platinum iridium wire, having an exposed outer end portion 319 terminating in a point 321. The outer end portion 319 of electrode 312 is coated with platinum black particles having a substantially uniform particle size and uniform distribution over the entire outer surface of end 319. The particles have uniform microscopic surfaces that are adapted to be located in intimate contact with the heart tissue to decrease electrical losses and increase the amplitude of the electrical signals picked up from the myocardium.

Wire 318 from body 314 to end 319 is enclosed within a sheath of medical grade rubber which electrically insulates the wire from the heart tissue. The inner end of wire 318 embedded within the rubber of body 314 is in electrical engagement with a first or inner conductor coil 324.

As shown in FIGS. 14 and 15, second electrode 328 is a metal member mounted on the bottom of body 314. Electrode 328, as seen in FIGS. 15, 16 and 17, has a pair of concentric rings 329 and 331 separated with an annular groove 343 to provide outer or contact surface of electrode 328 with a nonflat configuration to increase the surface area of the electrode that contacts the heart tissue. Rings 329 and 331 and groove 343 are also concentric with the first electrode 312. As seen in FIGS. 17 the bottom surface forming groove 343 is coated with platinum black particles 344. The coating can be platinum or platinum iridium or other electrically conductive materials. All of the outer surfaces of electrode 328 can be coated with platinum black particles, platinum, or iridium. Platinum black particles increase the surface areas of the electrode 328 that contact the heart tissue and provides for effective sensing vector in all directions.

Figure 18:
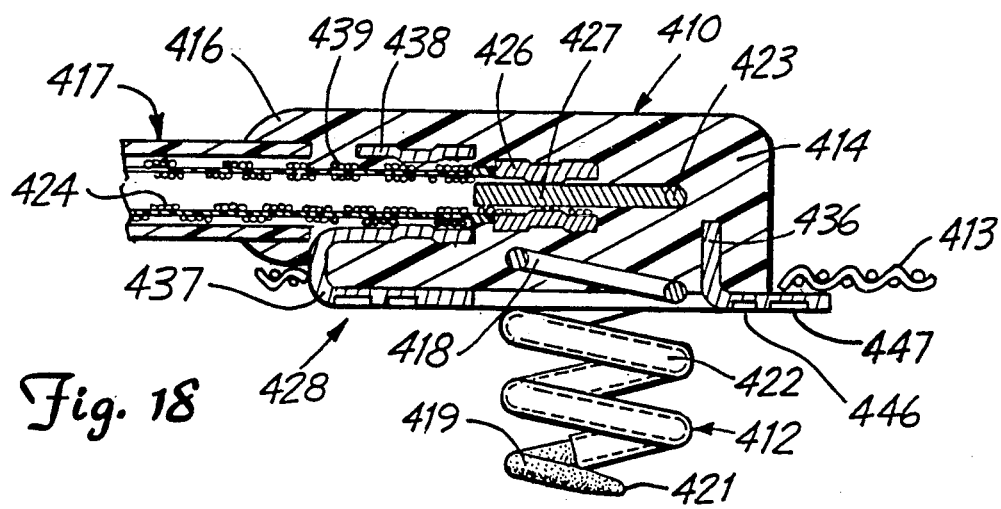
FIG. 18 is a sectional view similar to FIG. 11 of a third modification of the bipolar cardiac lead of the invention.
Figure 19:
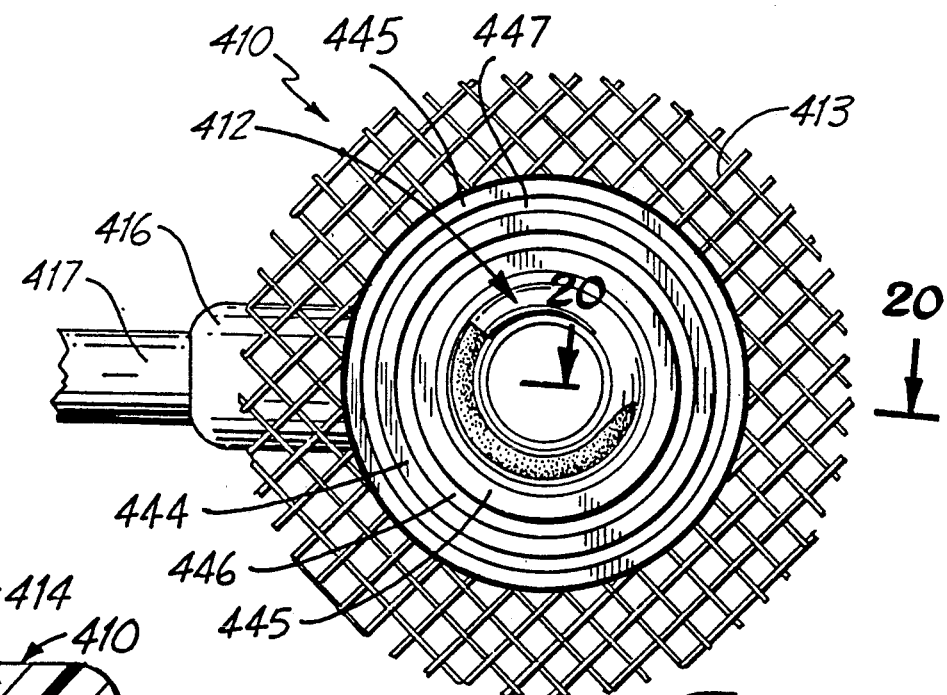
FIG. 19 is a bottom view of the distal end of the lead of FIG. 18.
Figure 20:
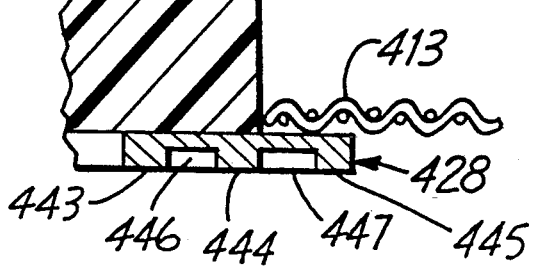
FIG. 20 is an enlarged sectional view taken along the line 20—20 of FIG. 19.

Referring to FIGS. 18 to 20, there is shown a third modification of the bi-polar lead indicated generally at 410. The parts of lead 410 that correspond to the parts of the lead 210 have the same reference numerals with the suffix 4 in lieu of 2. The anode or second electrode 428 has three concentric rings 443, 444 and 445 and a pair of concentric grooves 446 and 447 located between the rings as shown in FIGS. 19 and 20. Rings 443, 444, and 445 and grooves 446 and 447 are also concentric with the first electrode 412. The grooves 446, 447 and rings 443, 444, 445 provide an irregular or nonflat surfaces which is locatable in intimate contact with the heart tissue. The rings 443, 444, 445 and grooves 446, 447 provide for increased surface areas so that a smaller electrode 428 can be used to sense heart signals. The bottom surfaces of the grooves 446, 447 can contain a coating of platinum black particles, platinum, or platinum iridium.

Figure 21:
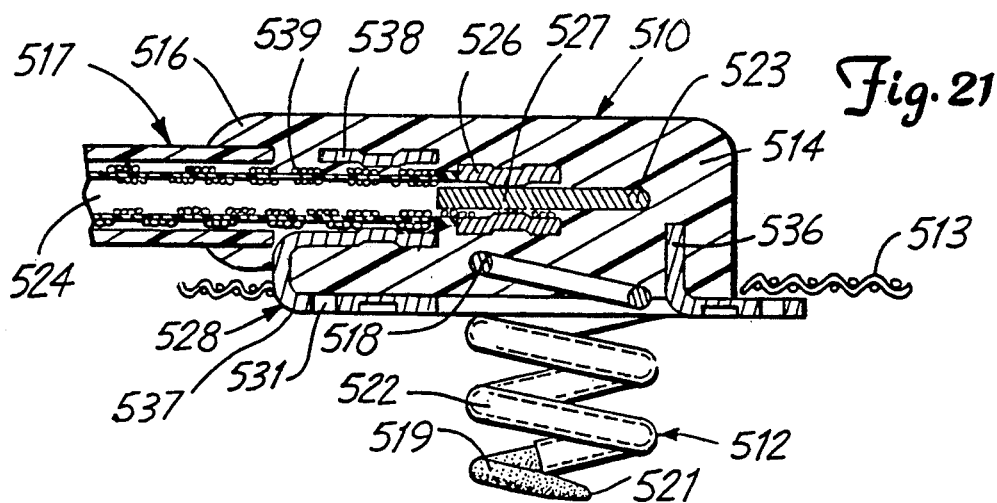
FIG. 21 is a sectional view similar to FIG. 11 of a fourth modification of the bipolar cardiac lead of the invention.
Figure 22:
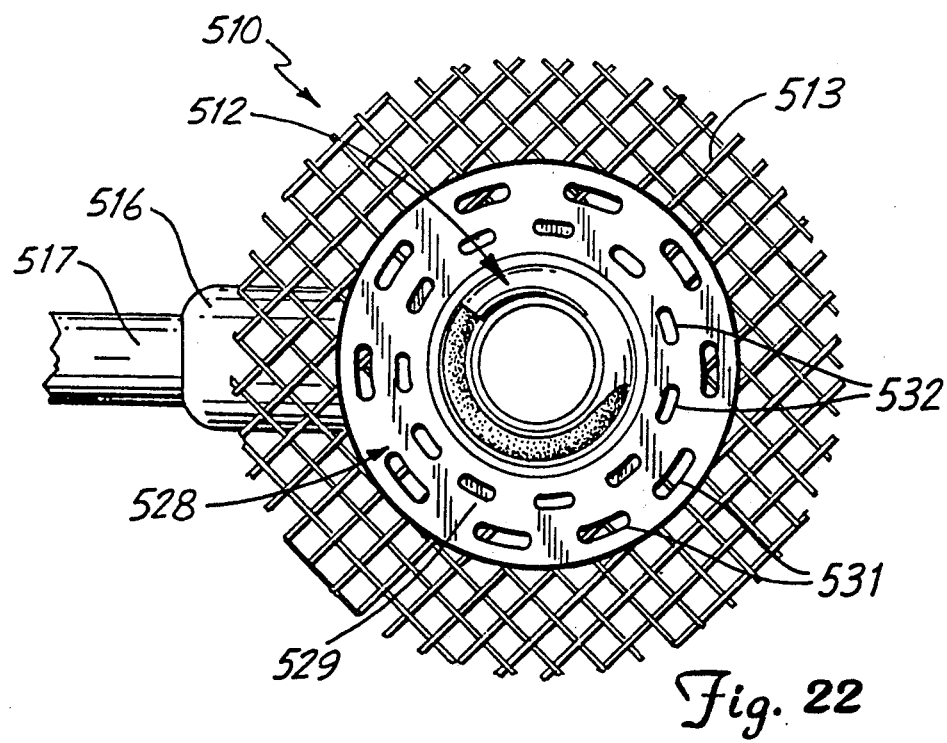
FIG. 22 is a bottom view of the distal end of the lead of FIG. 21.

Referring to FIGS. 21 and 22 there is shown a fourth modification of the bi-polar lead indicated generally at 510. The parts of lead 510 that correspond to the parts of lead 210 have the same reference numbers with the suffix 5 in lieu of 2.

Lead 510 has an anode or second annular electrode 528 attached to the bottom surface of head 514. Electrode 528 surrounding the helical electrode 512 has an annular exposed or outer surface 529 concentric with the axis of helical electrode 512. Electrode 528 is a metal member having a plurality of rings of holes 531 and 532 as seen in FIG. 22. Holes 531 and 532 are located in two concentric circles and are alternately spaced from each other. The holes 531 and 532 provide the electrode 528 with a nonflat or irregular surfaces thereby increasing the total surface area of the electrode that engages the heart tissue. The surface 529 can be coated with platinum black particles, platinum and platinum iridium or other surface treatments to enhance the electro-tissue interface between electrode 528 and heart tissue.

Referring to FIGS. 23 to 25, there is shown a fifth modification of the bi-polar lead indicated generally at 610. The parts of lead 610 that correspond to the parts of lead 210 have the same reference numbers with the suffix 6 in lieu of 2. Lead 610 has an annular electrode or anode 628 surrounding the helical electrode or cathode 612. The electrode 628 is secured to the bottom surface of a head 614. Electrode 628 has an exposed or outer surface 629. An annular ring 631 is secured by sentering or other means to the midsection of surface 629. Ring 631 is concentric with the helical electrode 612 as seen in FIGS. 24. Ring 631 as shown in FIGS. 23 has a circular cross section. Ring 631 can have alternative cross sections including but not limited to square, rectangular, or triangular. Referring to FIG. 25, electrode 628 is provided with an annular groove 632 to accommodate the ring 633. Ring 633 is secured by centering and the like to the metal of electrode 629. The outer or exposed surfaces of electrode 629 and rings 631 and 633 can be coated with platinum black particles, platinum or platinum iridium to further increase the surface areas of the electrode 628 that is located in intimate contact with the heart tissue and enhance the electro-tissue interface between electrode 628 and heart tissue.

Figure 26:
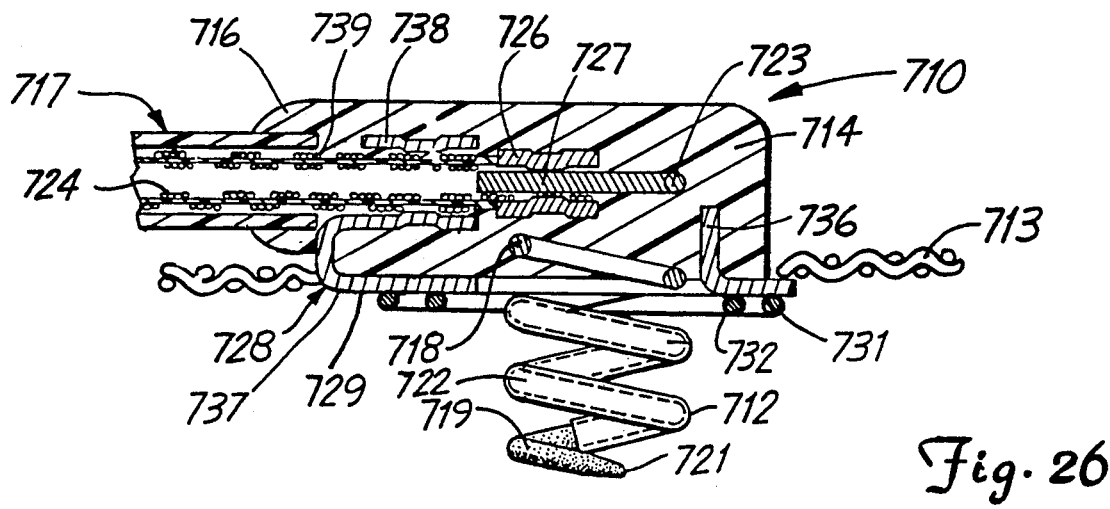
FIG. 26 is a sectional view similar to FIG. 11 of a sixth modification of the bipolar cardiac lead of the invention.
Figure 27:
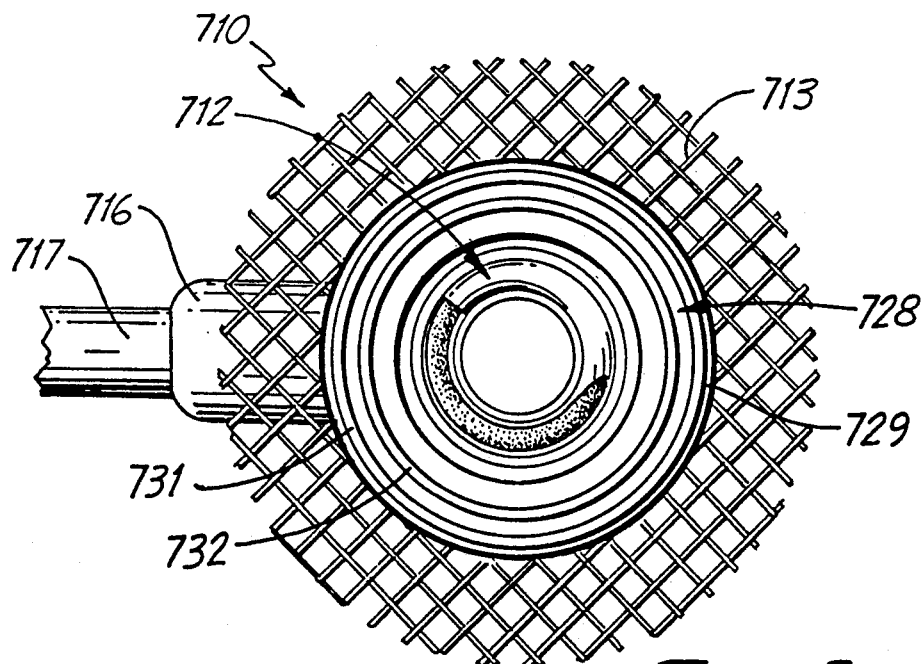
FIG. 27 is a bottom view of the distal end of the lead of FIG. 26.

Referring to FIGS. 26 and 27, there is shown a sixth modification of the bi-polar lead indicated generally at 710. The parts of lead 710 that correspond to the parts of lead 210 have the same reference numeral with the suffix 7 in lieu of 2. Lead 710 has an annular electrode or anode 728 that surrounds the helical electrode or cathode 712. Electrode 728 is attached to the bottom of head 714 and has an exposed or outer surface 729. A pair of concentric rings 731 and 732 are secured to surface 729 to provide the annular electrode with a nonflat or irregular configuration that is adapted to be placed in intimate contact with the heart tissue. Rings 731 and 732 are concentric with the axis of helical electrode 712 and have circular cross sections as shown in FIGS. 26. Rings 731 and 732 can have alternative cross sections including but not limited to square, rectangular, or triangular. Surface 729 as well as the outer surfaces of rings 731 and 732 provide nonflat or irregular surfaces that contact the heart tissue to provide an increased surface area as compared to a substantially flat surface with the results of decreased electrical losses and increased amplitude of the electrical signals from the heart tissue. The surface 729 as well as the outer surface of rings 731 and 732 can be coated with platinum black particles, platinum, or platinum iridium.

Figure 28:
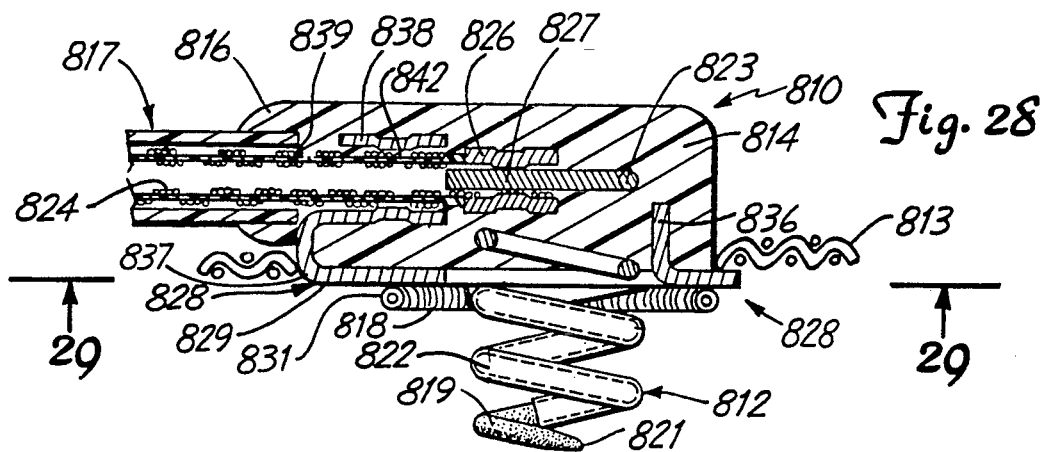
FIG. 28 is a sectional view similar to FIG. 11 of a seventh modification of the bipolar cardiac lead of the invention.
Figure 29:
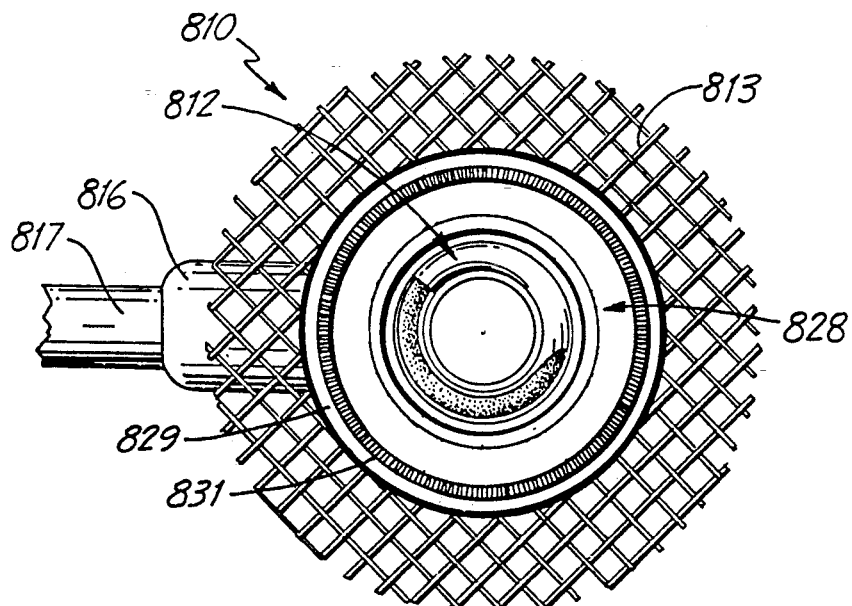
FIG. 29 is a bottom view of the distal end of the lead of FIG. 28.

Referring to FIGS. 28 and 29, there is shown a seventh modification of the bi-polar lead indicated generally at 810. The parts of lead 810 that correspond to the parts of lead 210 have the same reference numerals with the suffix 8 in lieu of 2. Lead 810 has a first electrode or cathode 812 shown as a helical or coil wire 818 attached to head 814. A second electrode 828 surrounding electrode 812 is also attached to head 814. Both electrodes 812 and 828 are electrically coupled to coaxial conductor 817. Electrode 828 has a support 829 having an outer surface adapted to engage heart tissue. A circular coil 831 is attached to support 829 in concentric relation with electrode 812. Coil 831 is a helical wire that may be coated with platinum black particles, platinum, or platinum iridium. The helical wire and surface of support 829 have nonflat or irregular surfaces adapted to be located in intimate surface contact with heart tissue. Heart tissue can also grow into the helical wire or coil 831.

While there have been shown and described preferred embodiments of the cardiac lead of the invention. It is understood that changes in the structure, arrangement of structure and materials may be made by those skilled in the art without departing from the invention. The invention is defined in the following claims.

We claim:

1. A cardiac lead connectable to a cardiac management device for transmitting electric current to and/or receiving electrical signals from the myocardium of the heart comprising: an elongated flexible conductor wire means, sheath means of non-electrical conductive material surrounding said conductor wire means, an electrical connector attached to the wire means adapted to be connected to a cardiac management device, a head of non-electrically conductive material connected to said conductor wire means and sheath means, a helical electrode having a first end section extended into said head and connected to said conductor wire means and a helical second end section extended from said head adapted to be screwed into the myocardium of a heart, said second end section having an outer helical surface terminating in a point, a layer of platinum black particles attached to the outer helical surface of the second end section, said layer of platinum black particles having substantially uniform particle size and uniform distribution on said outer surface of the second end section of the electrode whereby said layer has a continuous and uniform microporous outer platinum black surface locatable in surface contact with the myocardium of the heart whereby said layer of platinum black particles decreases electrical losses at the electrode-tissue interface, establishes intimate contact between the electrode and myocardium, and maximizes voltage applied to said myocardium and lowers stimulation thresholds and increases amplitude of sensed electrical signals from the myocardium; a second electrode including a porous wire mesh secured to the support means surrounding the helical electrode engagable with the myocardium of the heart around the helical electrode when the helical electrode is attached to the myocardium, support means holding the second electrode on the head, and a second elongated flexible conductor wire connected to the support means located within the sheath means and electrically insulated from the first elongated flexible conductor wire means.

2. The lead of claim 1 including: porous means secured to the head surrounding said helical second end section to enhance fibrotic growth to connect the head and second end section to the myocardium.

3. The lead of claim 2 wherein: the porous means is a generally circular shaped fabric secured to the head.

4. The lead of claim 1 including: sheath means of non-electrically conductive material extended from said head covering a portion of the helical second section of said electrode, said second section having an end portion projected from said sheath means, said end portion having an outer surface covered with said platinum black particles.

5. The lead of claim 1 including: sheath means of non-electrical conductive material joined to the head covering a portion of the helical second section of said electrode, said helical electrode having about one half turn end portion extended from said sheath, said end portion having an outer surface covered with said platinum black particles.

6. The lead of claim 1 wherein: the wire mesh has a coating of platinum black particles, platinum, Pyrolite carbon or titanium nitride.

7. The lead of claim 1 wherein: the support means comprises an electrical conductor attached to the head, said electrical conductor having an irregular surface configuration adapted to engage heart tissue.

8. The lead of claim 7 wherein: said electrical conductor includes ring means surrounding the helical electrode mounted on the head, porous wire mesh being secured to the ring means.

9. The lead of claim 7 wherein: the electrical conductor is an annular member having an exterior surface having at least one groove.

10. The lead of claim 9 wherein: at least part of said exterior surface has a coating of platinum black particles, platinum, Pyrolite carbon, or titanium nitride.

11. The lead of claim 1 including: a fabric member secured to the head to enhance fibrotic growth to secure the head to the myocardium.

12. A cardiac lead connectable to a cardiac management device for transmitting electric current to a heart and/or receiving electrical signals from the heart comprising: an elongated flexible conductor means, sheath means of non-electrically conductive material surrounding said conductor means, an electrical connector attached to the conductor means adapted to be connected to a cardiac management device, a head of non-electrical conductive material connected to said conductor means and sheath means, a first electrode means having a first section extended into said head and connected to said conductor means and a second section extended from said head adapted to be placed in engagement with heart tissue, said second section having an end portion with an outer surface, and a second electrode surrounding the first electrode connected to said conductor means, and said second electrode having an outer surface adapted to contact heart tissue when the second section of the first electrode is in engagement with heart tissue, said outer surface of the second electrode having an irregular surface configuration larger than the outer surface of the end portion of the first electrode.

13. The lead of claim 12 including: means on at least one of the surfaces of the first and second electrodes to enhance the electrical tissue interface between the surfaces of the first and second electrodes and heart tissue.

14. The lad of claim 13 wherein; the means to enhance the electrical tissue interface includes a coating of platinum black particles, platinum, Pyrolite carbon, or titanium nitride.

15. The lead of claim 13 wherein: the means to enhance the electrical tissue interface includes a layer of platinum black particles attached to the outer surface of the end portion of the second section of the first electrode and the outer surface of the second electrode, said layer of platinum black particles having substantially uniform particle size and uniform distribution on said outer surfaces whereby said layer has a continuous and uniform microporous outer platinum black surface locatable in surface contact with the heart tissue whereby said layer of platinum black particles decreases electrical losses at the electrical-tissue interface, established intimate contact between the electrode and heart tissue, maximize voltage applied to said heart tissue and lowers stimulation thresholds and increases amplitude of sensed electrical signals from the heart tissue.

16. The lead of claim 12 including: a generally circular fabric netting secured to the head.

17. The lead of claim 12 wherein: the second electrode comprises an annular support of electrically conductive material secured to the head, and at least one coiled wire conductor secured to the support adapted to engage heart tissue.

18. The lead of claim 12 wherein: the second electrode comprises an annular member of electrically conductive material secured to said head, said member having an outer surface and at least one groove in the outer surface.

19. The lead of claim 12 wherein: the second electrode comprises an annular member of electrically conductive material having a plurality of holes.

20. The lead of claim 12 wherein: the second electrode comprises an annular member of electrically conductive material having an outer surface, an at least one circular conductor member secured to said outer surface.

21. The lead of claim 12 wherein: the second electrode comprises an annular member of electrically conductive material having spaced concentric rings, a plurality of circumferentially spaced spokes connected to the rings, and a plurality of grooves located between the rings, said irregular surface configuration of the outer surface of the second electrode comprising outer surfaces of the rings and spokes and the bases of the grooves.

22. A cardiac lead connectable to a cardiac management device for transmitting electric current to a heart and/or receiving electrical signals from the heart comprising: an elongated flexible conductor means, sheath means of non-electrically conductive material surrounding said conductor means, an electrical connector attached to the conductor means adapted to be connected to a cardiac management device, a head of non-electrical conductive material connected to said conductor means and sheath means, a first electrode having a first section extended into said head and connected to said conductor means and a second section extended from said head adapted to be placed in engagement with heart tissue, said second section having an end portion with an outer surface, and a second electrode surrounding the first electrode connected to said conductor means, said second electrode having an outer surface adapted to contact heart tissue when the second section of the first electrode is in engagement with heart tissue, said outer surface of the second electrode having an irregular surface configuration larger than the outer surface of the end portion of the first electrode, the second electrode comprises an annular support of electrically conductive material secured to the head, and a porous wire mesh conductor secured to the support.

23. A cardiac lead connectable to a cardiac management device for transmitting electric current to and/or receiving electrical signals from the myocardium of the heart comprising: an elongated flexible first conductor means adapted to be connected to the cardiac management device, sheath means of non-electrically conductive material surrounding said conductor means, a head of non-electrically conductive material attached to the conductor means and sheath means, a helical electrode having a first end section extended into said head and connected to said conductor means and a helical second end section extended from said head adapted to be screwed into the myocardium of a heart, a second electrode surrounding the helical electrode, said second electrode including a porous wire mesh electrical conductor engageable with the myocardium of the heart around the helical electrode when the helical electrode is screwed into the myocardium, support means mounted on the head holding the second electrode on the head, and a second elongated flexible conductor means conductively connected to said second electrode located within the sheath means and electrically insulated from the first conductor means.

24. The lead of claim 23 wherein: the wire mesh conductor has a coating platinum black particles, platinum, Pyrolite carbon or titanium nitride.

25. The lead of claim 23 wherein: the support means comprises an annular electrical conductor attached to the head, said wire mesh conductor being secured to said annular electrical conductor.

26. The lead of claim 23 including: a fabric netting secured to the head to enhance fibrotic growth to secure the head to heart tissue.

27. A cardiac lead connectable to a cardiac management device for transmitting electric current to and/or receiving electrical signals from the myocardium of the heart comprising: an elongated flexible first conductor means, sheath means of non-electrically conductive material surrounding said conductor means, and electrical connector attached to the conductor means adapted to be connected to a cardiac management device, a head of non-electrical conductive material connected to said conductor means and sheath means, a first electrode having a first end section extended into said head and connected to said conductor means and a second end section extended from said head adapted to be placed into engagement with heart tissue, a second electrode attached to the head surrounding the first electrode engagable with heart tissue when the first electrode is placed into engagement with heart tissue, said second electrode having annular outer surface means including means having irregular surfaces adapted to engage heart tissue, and elongated flexible second conductor means conductively connected to the connector and said second electrode located within the sheath means and electrically insulated from the first conductor means.

28. The lead of claim 27 including: a fabric netting secured to the head to enhance fibrotic growth to secure the head to the heart tissue.

29. The lead of claim 27 wherein: the means having irregular surfaces comprise an annular member and at least one circular coiled conductor secure to the annular member.

30. The lead of claim 27 wherein: the means having irregular surfaces comprise at least one groove in the second electrode.

31. The lead of claim 27 wherein: the means having irregular surfaces comprises an annular member and at least one circular member secured to the annular member.

32. The lead of claim 27 wherein: the means having irregular surfaces comprises an annular member having a plurality of grooves.

33. The lead of claim 27 wherein: the means having irregular surfaces comprises an annular member having a plurality of holes.

34. The lead of claim 33 wherein: the second electrode has a coating of platinum black particles, platinum, pyrolite carbon or titanium nitride.

35. The lead of claim 33 including: means on the second end section of the helical electrode to enhance the electrical tissue interface between the second end section and the heart tissue.

36. The lead of claim 35 wherein: the means to enhance the electrical tissue interface including a coating of platinum black particles, platinum, Pyrolite carbon, or titanium nitride.

37. The lead of claim 27 wherein: the means having irregular surfaces comprise a member having spaced concentric rings, at least one spoke connected to the rings, and a plurality of grooves located between the rings, said irregular surfaces comprising outer surfaces of the rings and spoke and surfaces at the base of the grooves.

38. The lead of claim 37 wherein: the member has a plurality of circumferentially spaced spokes connected to the rings.

39. A cardiac lead connectable to a cardiac management device for transmitting electrical current to and/or receiving electrical signals from the myocardium of the heart comprising: an elongated flexible first conductor means, sheath means of non-electrically conductive material surrounding said conductor means, and electrical connector attached to the conductor means adapted to be connected to a cardiac management device, a head of non-electrical conductive material connected to said conductor means and sheath means, a first electrode having a first end section extended into said head and connected to said conductor means and a second section extended from said head adapted to be placed into engagement with heart tissue, a second electrode attached to the head surrounding the first electrode engagable with heart tissue when the first electrode is placed into engagement with heart tissue, said second electrode having annular outer surface means including means having irregular surfaces adapted to engage heart tissue, and elongated flexible second conductor means conductively connected to the connector and said second electrode located within the sheath means and electrically insulated from the first conductor means, the means having irregular surfaces comprise a porous wire mesh electrical conductor.

40. A cardiac lead connectable to a cardiac management device for transmitting electric current to and/or receiving electrical signals from the myocardium of the heart comprising: an elongated flexible first conductor means adapted to be connected to the cardiac management device, sheath means of non-electrically conductive material surrounding said conductor means, a head of non-electrically conductive material attached to the conductor means and sheath means, a helical electrode having a first end section extended into said head and connected to said conductor means and a helical second end section extended from said head adapted to be screwed into the myocardium of a heart, a second electrode secured to the head surrounding the helical electrode, said second electrode including a member of electrically conductive material having spaced concentric rings and at least one spoke connected to the rings having first outer surfaces and grooves between the rings, said member having second outer surfaces at the bases of the grooves, said first and second outer surfaces being engageable with the myocardium of the heart around the helical electrode when the helical electrode is screwed into the myocardium, and a second elongated flexible conductor means conductively connected to said second electrode located within the sheath means and electrically insulated from the first conductor means.

* * * * *